United States Patent [19]

Haber et al.

[11] Patent Number: 5,067,948
[45] Date of Patent: Nov. 26, 1991

[54] SAFETY, PACKAGING, INJECTION AND DISPOSAL SYSTEM FOR PRE-FILLED PHARMACEUTICAL VIALS

[75] Inventors: Terry M. Haber, Lake Forest; Clark B. Foster, Laguna Niguel, both of Calif.

[73] Assignee: Habley Medical Technology Corporation, Laguna Hills, Calif.

[21] Appl. No.: 589,133

[22] Filed: Sep. 27, 1990

[51] Int. Cl.$^5$ .............................................. A61M 5/178
[52] U.S. Cl. .................... 604/213; 604/232; 604/192; 604/205; 604/220; 604/225
[58] Field of Search .............. 604/21, 93, 118, 121, 604/181, 182, 183, 184, 187, 192, 197-201, 204, 205, 218, 220, 225-226, 231-234, 86, 87, 88, 259, 213, 236, 237; 81/3.25

[56] References Cited

U.S. PATENT DOCUMENTS

| | | | |
|---|---|---|---|
| 2,453,590 | 11/1946 | Poux | 604/201 |
| 2,708,438 | 11/1951 | Cohen | 604/192 |
| 3,563,373 | 2/1971 | Paulson | 604/197 |
| 3,583,263 | 6/1971 | Herigstad | 81/3.25 |
| 4,084,606 | 4/1978 | Mittelson | 604/237 |
| 4,244,378 | 1/1981 | Brignola | 604/201 |
| 4,303,069 | 12/1981 | Cohen | 604/192 |
| 4,758,231 | 7/1988 | Haber et al. | 604/198 |
| 4,861,335 | 8/1989 | Reynolds | 604/88 |
| 4,934,379 | 6/1990 | Marzolf et al. | 604/231 |
| 4,950,253 | 8/1990 | Jacobs | 604/218 |
| 4,958,622 | 9/1990 | Selenke | 604/192 |

FOREIGN PATENT DOCUMENTS 873459  6/1971 Canada .................. 128/88

Primary Examiner—C. Fred Rosenbaum
Assistant Examiner—Chalin Smith
Attorney, Agent, or Firm—Townsend and Townsend

[57] ABSTRACT

A vial holding syringe (84) includes a barrel (6) having a bore (12), a sealable needle end (8) and an open plunger end (10). A plunger (16) is mounted within the bore and includes an elongated hollow stem (18), having an interior (36) sized to hold a conventional vial (4), and a piston (20). The stem includes a hollow piercing member (46) having a piercing end (48), opposite the membrane (42) covering the vial, and an outer end (50), adjacent a one-way valve (70) to permit passage of the medication (80) within the vial from the vial, through the hollow piercing member and through the one-way valve into a variable volume region (67) of the bore between the needle end of the barrel and the piston. An opening (14) at the needle end of the barrel is initially sealed by a cap (66). To use, the plunger is pulled part way from the bore to create a partial vacuum within the variable volume region. During this process, the diaphragm of the vial is driven onto the piercing end of the piercing member. This causes the contents of the vial to be expelled from the vial and into the variable volume region under the influence of the partial vacuum formed within the variable volume region. The cap is then removed, a hollow needle (82) is mounted to the barrel and the injection is given.

13 Claims, 3 Drawing Sheets

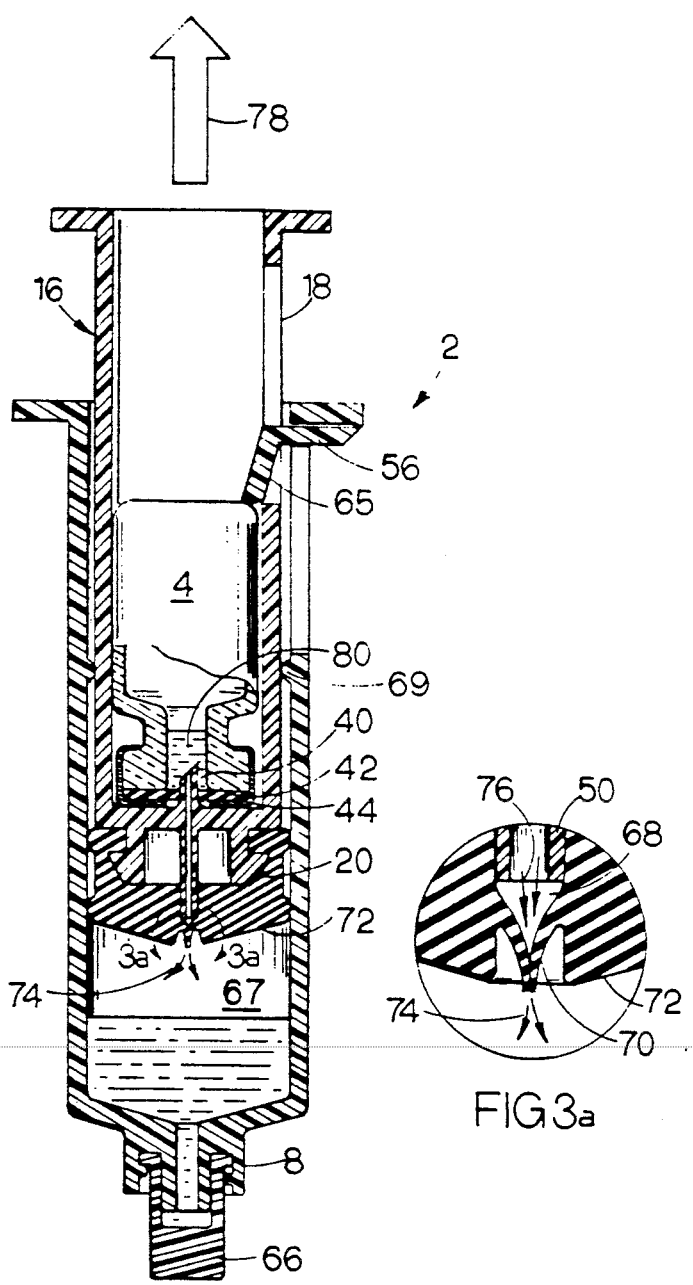
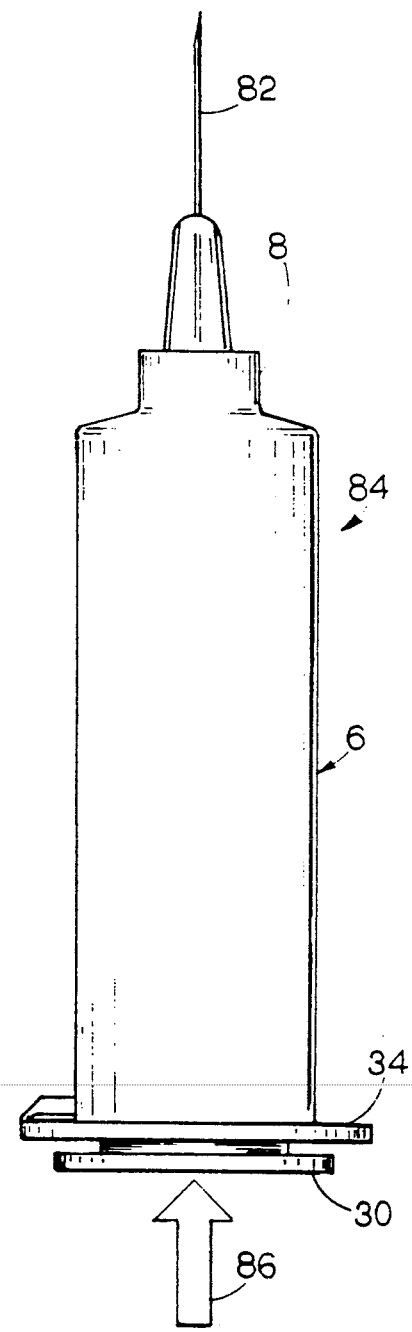
FIG.3  FIG.3a  FIG.4

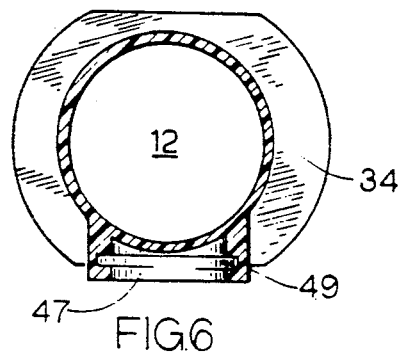
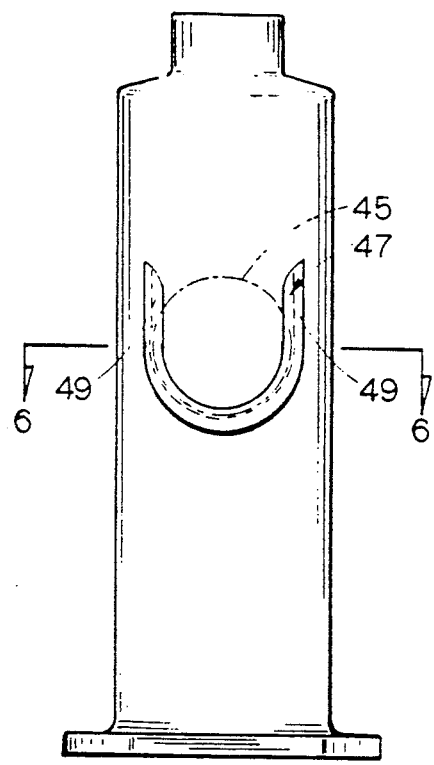
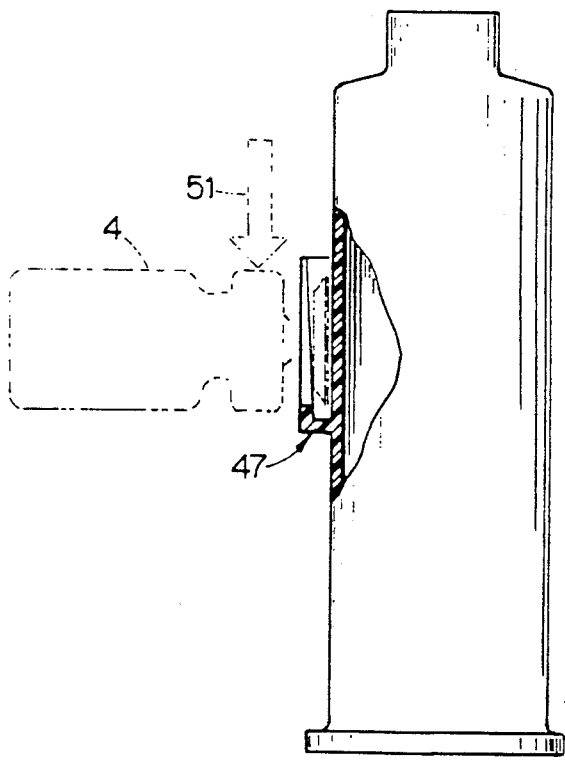

SAFETY, PACKAGING, INJECTION AND DISPOSAL SYSTEM FOR PRE-FILLED PHARMACEUTICAL VIALS

CROSS REFERENCE TO RELATED APPLICATIONS

This invention is related to U.S. patent application Ser. No. 558,878, filed July 27, 1990 for MULTIPLE-CELLED SAFETY PACKAGE, NEEDLE GUARD AND SAFE DISPOSAL MODULE FOR PRE-FILLED MEDICATION CARTRIDGES; and U.S. patent application Ser. No. 07/588,773, filed concurrently with this application for SAFETY PACKAGING, INJECTION AND DISPOSAL SYSTEM FOR PRE-FILLED PHARMACEUTICAL AMPULES, the disclosures of which are incorporated by reference.

BACKGROUND OF THE INVENTION

Medication intended for injection into the patient is often stored in vials. Vials are small, typically glass, containers having an open mouth covered by a rubber membrane or diaphragm. The rubber diaphragm is held in place by a metal ring. The rubber diaphragm is initially covered by a cap which is removed prior to use, typically with a flicking action of one's thumb. Presently, the usual procedure for drawing medicine into a syringe for subsequent injection into a patient involves the following steps: (1) The diaphragm of the vial containing medication is cleaned, usually with an alcohol swab; (2) A capped or sheathed needle is affixed to a syringe and the needle's sheath is removed; (3) The vial is often inverted so that the medicine is in contact with the diaphragm; (4) Frequently, an amount of air approximately equal to the amount of medication intended to be drawn up is then aspirated into the syringe; (5) The needle is inserted through the diaphragm into the vial; (6) The air that was aspirated into the syringe is pushed into the vial to prevent a vacuum that would make it more difficult to draw up the medicine; (7) The medicine is aspirated into the syringe; (8) The needle is removed from the vial; (9) The medicine is either injected into the patient or the needle is recapped for later injection.

Some potential problems with preparing medications for injection are contamination of the medication and accidental injury from the needle. Needle injuries generally involve puncturing one's finger during manipulation of the syringe and vial or while recapping the needle.

SUMMARY OF THE INVENTION

The present invention is directed to a syringe which contains within it a generally conventional vial of medicine, the medicine within the vial being accessed by the manipulation of the syringe without exposing the diaphragm covering the mouth of the vial to contamination.

The vial holding syringe includes a barrel having a bore, a sealable needle end and an open plunger end. A plunger is mounted for reciprocal movement within the bore of the barrel at the plunger end. The plunger includes an elongated hollow stem having an interior sized to hold a conventional vial. A piston is mounted to the inner end of the stem and seals the plunger within the bore of the barrel.

The stem includes a hollow piercing member having an inner, piercing end extending into the interior of the stem to a position opposite the diaphragm covering the vial mouth. The outer end of the piercing member is positioned adjacent a one-way valve to permit passage of the medication within the vial from the vial, through the hollow piercing member, through the one-way valve and into a variable volume region of the bore defined between the needle end of the barrel and the piston. Preferably, the one-way valve is formed as an integral part of the piston. An opening at the needle end of the barrel opens into the variable volume region. This opening is preferably initially sealed by a cap mounted to the needle end of the barrel.

To activate the syringe with the vial in place, the health care worker draws the plunger from a depressed position, with the piston adjacent the inner end, to a retracted position, with the piston spaced apart from the inner end. This creates a partial vacuum within the variable volume region. During this process, the diaphragm-covered end of the vial is driven onto the piercing end of the piercing member. This is accomplished, in the preferred embodiment, through the use of a vial stop carried by the barrel at the plunger end of the barrel. The vial stop extends through a longitudinal slot formed towards the outer end of the stem, and into the hollow interior of the stem into the path of the vial. The contents of the vial are expelled from the vial and into the variable volume region under the influence of the partial vacuum formed within the variable volume region. After the medication has been transferred from the vial to the variable volume region of the bore, the cap is removed, a hollow needle is mounted to the needle end of the barrel. The sheath covering the needle can be removed so the medicine can be injected or the syringe, with the needle sheathed, can be set aside for later use.

One of the primary advantages of the invention is that it permits medication to be packaged with, or at least carried by, its delivery system, that is the syringe. This not only enhances cleanliness and sterility, but also promotes good inventory control within a medical setting. This is especially true in situations in which an automatic packaging and inventory control system is used to monitor the supply, distribution and use of various medications and medical devices, such as syringes.

Although the present invention is particularly well suited for use with a vial housed within the stem of the syringe, so that the syringe acts as both the syringe and the packaging, the invention may be used in situations in which the health care worker inserts a vial into the interior of the stem before use. Although doing so may require cleaning of the diaphragm prior to insertion into the stem, it still eliminates the need to manually draw the medicine from the vial into the syringe through the needle. However, since the plastic protective cap covering the diaphragm can be removed immediately before inserting the vial into the stem, the diaphragm may be sufficiently clean to eliminate the need to clean the diaphragm before use.

The present invention is advantageous because it offers greater efficiency with less manipulation. Its fewer steps permit increased speed of preparation and fewer chances of contamination or accidental "finger sticks". These advantages may be particularly helpful if the person preparing the injection has minimal training. For example, a patient or a family member may administer medications in a prescribed regimen at home. Additionally, a patient who practices self administration of medications may have physical disabilities that would magnify the importance of having fewer steps to perform. For example, patients suffering difficulties with arthritis, decreased visual acuity, or senile tremors may find any increased simplicity of administration a great benefit.

Additionally, these advantages may be important in other clinical settings. For example, clinics performing frequent immunizations and emergency rooms may find the greater safety and efficiency offered by the present invention especially helpful.

Although the present invention is particularly well suited for single use situations, it can also be used for multiple injections with a single patient as well. In such cases, after an injection the hollow needle can be removed from the needle end of the barrel and the opening at the needle end can be resealed using a seal-producing cap. For reuse, the cap is removed and a new, sterile hollow needle is mounted to the needle end of the barrel and the next injection is given.

It is preferred that the barrel and stem both be transparent to permit the health care worker to view the amount of medication within the variable volume region. This helps to ensure that the medication has properly been transferred from the vial to the variable volume region. In addition, especially under multiple use situations, the barrel can be graduated to permit the health care worker to inject the proper amount of medication. Making the stem transparent permits the health care worker to double-check any identification markings on the vial to be sure that they match with any identification markings on the syringe itself.

Other features and advantages of the invention will appear from the following description in which the preferred embodiments have been set forth in detail in conjunction with the accompanying drawings

BRIEF DESCRIPTION OF THE DRAWINGS

FIG. 3 illustrates the syringe structure of FIG. 2 with a plunger in the retracted position and showing the transfer of the contents of the vial from the vial to the variable volume region adjacent the needle end of the barrel;

FIG. 3A is an enlarged view of the one-way valve formed by the piston;

FIG. 4 is an outside elevational view of the syringe structure of FIGS. 2 and 3 with a hollow needle mounted to the needle end of the barrel after the plunger has been moved from the retracted position of FIG. 3 to a post use depressed position.

FIG. 5 is a front elevational view of an alternative embodiment of the barrel of FIG. 1 including a protective cap retainer and showing a removed protective cap in dashed lines;

FIG. 6 is a top view of the barrel of FIG. 5 taken along line 6—6; and

FIG. 7 is a right-side elevational view of the barrel of FIG. 5 illustrating the movement of a vial, shown in dashed lines, used to remove the protective cap.

DESCRIPTION OF THE PREFERRED EMBODIMENT

Figures 1, 2:
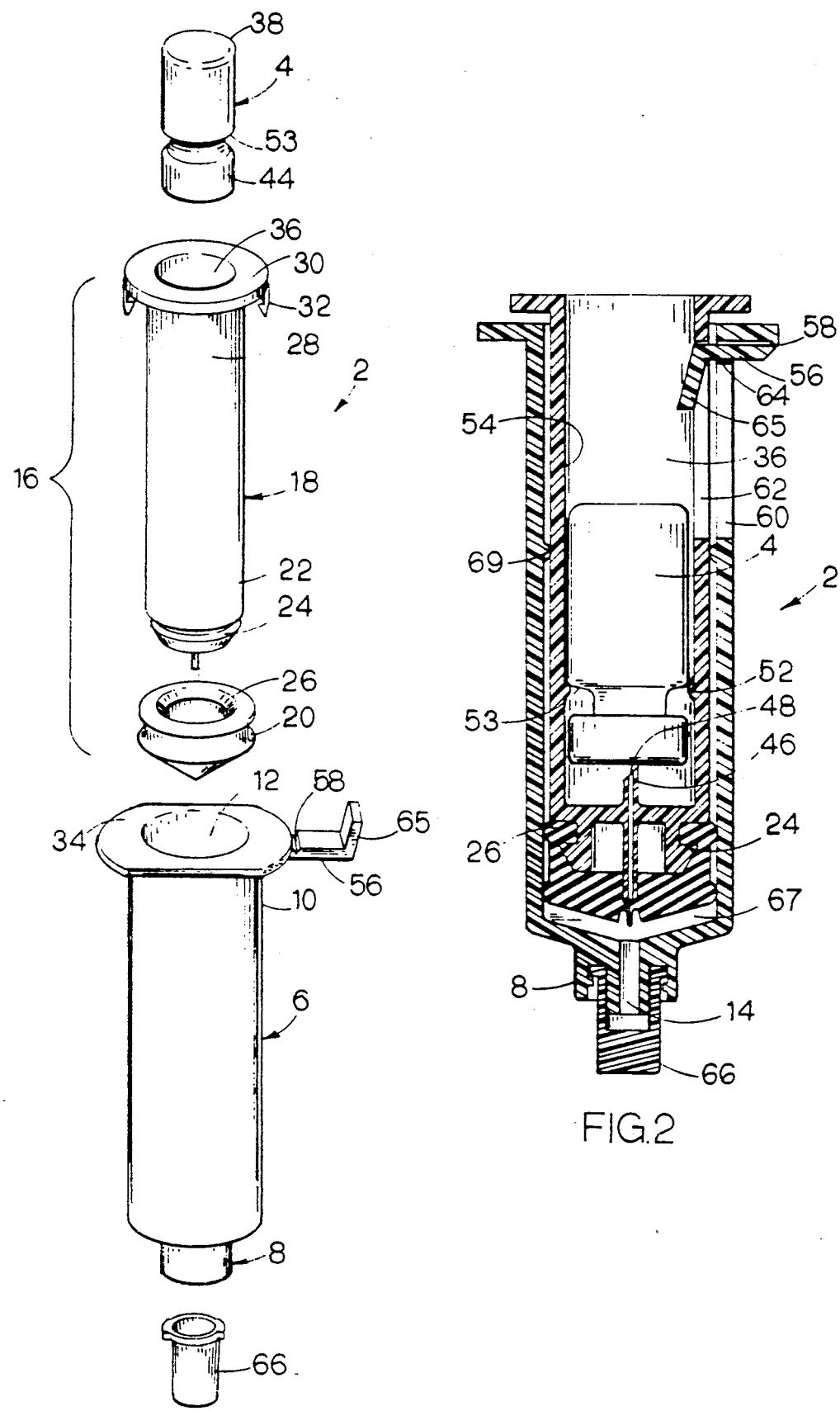
FIG. 1 is an exploded isometric view of a vial holding syringe structure made according to the invention.
FIG. 2 is an assembled view of the syringe structure of FIG. 1 shown in an as-packaged condition with the plunger in the depressed position.

FIG. 1 shows a syringe structure 2 configured to hold a vial 4 and automatically access the contents of the vial for use. Structure 2 includes a barrel 6 having a needle end 8 and a plunger end 10. Barrel 6 defines an axial bore 12 completely opened at plunger end 10. Bore 12 is also fluidly connected to an opening 14, see FIG. 2, formed at needle end 8. Structure 2 also includes a plunger 16, the plunger including a stem 18 and a piston 20. Stem 18 has an inner end 22 with an outwardly extending flanged lip 24, seen best in FIG. 2, sized to engage an inwardly extending flanged lip 26 of piston 20. Barrel 6 and stem 18 are preferably of a clear, medically compatible plastic material, such as polypropylene, while piston 20 is a medically compatible elastomeric material, such as rubber. Piston 20 and stem 18 could be a one-piece molded structure as well. Piston 20 is sized to provide plunger 16 a good seal with bore 12.

Stem 18 includes an outer end 28 having an enlarged flange 30 at the outer end. Flange 30 has a pair of resilient locking fingers 32 formed to engage beneath a similarly positioned flange 34 at plunger end 10 of barrel 6 following use, as is described below.

Stem 18 also includes a hollow interior 36 within which vial 4 is placed. Vial 4 is preferably a conventional vial used to contain medicine and has a glass body 38 forming a mouth 40, seen in FIG. 3, covered by a rubber diaphragm 42. Diaphragm 42 is held in position in a conventional manner by a metal ring 44. Commercially available vials 4 typically include a protective cap 45, see FIGS. 5–7, which is removed prior to use. Such a cap, if originally found on vial 4, is removed prior to placing vial 4 within interior 36.

One way to remove protective cap 45 is through the use of a protective cap retainer 47. As suggested in FIG. 7, cap 45 is removed by first placing cap 45 between the opposed legs 49 of retainer 47 and moving vial 4 in the direction of arrow 51. Legs 49 are tapered, thinner at the top than at the bottom as shown in FIG. 7, so to pull cap 45 from mouth 40. The wedging action of legs 49 hold cap 45 in place during subsequent use of the syringe. This greatly simplifies the procedure used to remove and dispose of the protective cap. The use of retainer 47 is especially useful when structure 2 is stored separately from vial 4, with vial 4 being inserted into interior 36 by the health care worker.

Stem 18 includes a piercing member 46, preferably formed as a unitary member with stem 18. Piercing member 46 includes an inner, piercing end 48 and an outer end 50. Vial 4 is positioned with diaphragm 42 near, but not touching, piercing end 48. This positioning is achieved through the snug fit of vial 4 within interior 36 and the use of projections 52 extending from the inner wall 54 of stem 18, which engage shoulders 53 of body 38 of vial 4. The snug fit is achieved through the use of one or more rings (69) projecting inwardly from inner wall to engage vial 4.

Barrel 6 includes a vial stop tab 56 molded as a one piece member and extending from flange 34 at a hinge 58. After vial 4 is positioned within interior 36, tab 56 is pivoted from the piston of FIG. 1 to the position of FIG. 2 about hinge 58 by passing through aligned longitudinal slots 60, 62 formed in barrel 6 and stem 18. Vial stop tab 56 is maintained in the position of FIG. 2 through the engagement of a pair of positioning projections 64 formed on either side of longitudinal slot 60 near flange 34. The outer end 65 of tab 56 is angled towards needle end 8 so that, if desired, vial 4 can be inserted into interior 36 after tab 56 is in the position of FIG. 2 since end 65 will be temporarily deflected outwardly by vial 4 being pushed into interior 36.

FIG. 2 illustrates syringe structure 2 as it may be stored and distributed with a cap 66 mounted to needle end 8 of barrel 6 to cover opening 14. Cap 66 is configured to mate with a conventional LUER-LOK ® syringe fitting used with many syringes. Sealing opening 14 maintains the variable volume region 67 within bore 12 between piston 20 and opening 14 sterile. Further, the outer surface of diaphragm 42 and piercing end 48 of piercing member 46 are also maintained in a sterile condition by an appropriate seal provided between inner wall 54 and vial 4. In a preferred embodiment, this seal is created by the one or more appropriately sized and shaped rings 69 projecting inwardly from inner wall 54 to engage vial 4 used to create the snug fit of vial 4 within interior 36. Other sealing methods can be used as well.

Outer end 50 of piercing member 46 extends into a hole 68 formed in piston 20. Hole 68 has a one-way valve 70 formed at one end adjacent the face 72 of piston 20. One-way valve 70 is a duck-bill type valve molded integrally with piston 20 and permits passage of fluid along hole 68 in the direction of arrows 74, 76, that is into variable volume region 67, but not in the reverse direction.

FIG. 3 illustrates the movement of plunger 16 from the pre-use, depressed position of FIG. 2 to a retracted position. At the retracted position, vial 4 moves upwardly with stem 18 until the vial contacts vial stop tab 56 as illustrated in FIG. 3. Further movement of stem 18 in the direction of arrow 78 causes vial 4 to overcome the resistance of projections 52 and be driven towards piston 26. Doing so causes piercing end 48 to pierce diaphragm 42 as shown in FIG. 3. The movement of plunger 16 to the retracted position of FIG. 3 causes a partial vacuum to be created within region 67. Cap 66 seals opening 16 sufficient to permit the partial vacuum to be created. Upon piercing diaphragm 42, the contents 80 of vial 4 quickly pass from vial 4, through piercing member 46, past valve 70 and into region 67 as suggested by arrows 74. At this point, syringe structure 2 is inverted to the orientation of FIG. 4, cap 66 is removed and a hollow needle 82 is mounted to needle end 8 to create a vial holding syringe 84. Syringe 84 is then used by depressing stem 18 as suggested by arrow 86.

In use, the health care worker takes syringe structure 2 of FIG. 2 and pulls on stem 18 in the direction of arrow 78 of FIG. 3 until plunger 16 is in the full retracted position of FIG. 3. This causes piercing end 48 of piercing member 46 to pierce diaphragm 42 allowing contents 80 of vial 4 to pass into variable volume region 67 under the influence of the partial vacuum formed within region 67. Syringe structure 2 is then inverted, cap 66 is removed and hollow needle 82 is mounted in its place. The injection is then given and syringe 84 is disposed of in a safe manner.

Syringe structure 2 is primarily intended for single use situations. Therefore, fully depressing stem 18 into bore 12 of barrel 6 causes fingers 32 to engage onto flange 34 thus locking plunger 16 to barrel 6. However, in appropriate cases the contents of vial 4 may be sufficient to provide more than one injection for a single patient. In such cases, between injections hollow needle 82 may be removed and a new, sterile hollow needle mounted to needle end 8 in its place. In such case, gradations on barrel 6 and/or stem 18, to indicate the amount of medication for each injection, would be useful.

In some circumstances it may be desirable to use syringe structure 2 for multiple injections but over a period of time, such as insulin injections. In such cases, a used needle 82 may be removed and replaced with a sterile cap 66 adapted to seal opening 14 so that the medication does not leak out through opening 14 between uses.

Vial 4 is shown positioned adjacent piercing end 48 when plunger 16 is in its pre-use, depressed position. If desired, vial 4 could be positioned near vial stop tab 56, or somewhere in between as well. Also, the invention could be carried out by piercing diaphragm 42 prior to withdrawing plunger 16. Other methods for driving vial 4 into piercing member 46, including driving an object down hollow interior 36, could be used.

Cap 66 could be eliminated in various ways. For example, needle 82 could be used with a sheath which provides an air-tight seal.

Other modifications and variations can be made to the disclosed embodiment without departing from the subject of the invention as defined in the following claims.

What is claimed is:

1. A vial holding syringe structure, the vial of the type having a pierceable membrane at one end, the syringe structure comprising:
   a barrel having a bore, a sealable needle end and a plunger end;
   a plunger including a stem, having inner and outer ends, and a piston sized to sealingly engage the bore, the plunger slidably mounted within the barrel at the plunger end for reciprocal movement between a depressed position, with the inner end towards the needle end, and a retracted position, with the inner end spaced apart from the needle end, the barrel and plunger defining a variable volume region at the needle end, a partial vacuum being created in the variable volume region when the plunger moves towards the retracted position;
   the stem having an interior sized to house the vial; and
   means for transferring the contents of the vial along a path to the variable volume region when the variable volume region is at the partial vacuum, the transferring means including a one-way valve along said path to permit the contents of the vial to flow into the variable volume region but not the reverse without any manipulation by the user, the one-way valve being formed as part of the piston;
   whereby the transferred contents of the vial in the variable volume region can be injected through a hollow needle, mounted to the needle end, by the manipulation of the plunger.

2. The syringe structure of claim 1 wherein the barrel has an opening, communicating with the variable volume region, at the needle end, and further comprising cap means for selectively sealing the opening.

3. The syringe structure of claim 1 wherein the piston seal includes a piston mounted to the inner end of the stem.

4. The syringe structure of claim 1 wherein the transferring means includes a hollow piercing member having a piercing end positioned within the interior of the stem opposite the pierceable membrane of the vial.

5. The syringe structure of claim 4 wherein the transferring means includes a vial stop mounted to the barrel and extending into the interior of the stem so to engage the vial when the plunger is moved towards the retracted position so the piercing end of the piercing member is driven through the pierceable membrane of the vial.

6. The syringe structure of claim 1 further comprising means for securing the plunger in the depressed position.

7. A vial holding syringe structure, the vial of the type having a pierceable membrane at one end, the syringe structure comprising:
 a barrel having a bore, a sealable needle end and a plunger end;
 a plunger including a stem, having inner and outer ends, and a piston seal sized to sealingly engage the bore, the plunger slidably mounted within the barrel at the plunger end for reciprocal movement between a depressed position, with the inner end towards the needle end, and a retracted position, with the inner and spaced apart from the needle end, the barrel and plunger defining a variable volume region at the needle end, a partial vacuum being created in the variable volume region when the plunger moves towards the retracted position;
 the stem having an interior sized to house the vial; and
 means for transferring the contents of the vial along a path to the variable volume region when the variable volume region is at the partial vacuum;
 the transferring means including:
 a hollow piercing member having a piercing end positioned within the interior of the stem opposite the pierceable membrane of the vial; and
 a vial stop mounted to the barrel and extending into the interior of the stem so to engage the vial when the plunger is moved towards the retracted position so the piercing end of the piercing member is driven through the pierceable membrane of the vial;
 whereby the transferred contents of the vial in the variable volume region can be injected through a hollow needle, mounted to the needle end, by the manipulation of the plunger.

8. The syringe structure of claim 7 wherein the vial stop includes a vial stop element, hingedly mounted to the barrel adjacent aligned openings in the barrel and the stem for movement between an internal position, extending into the interior of the stem, and an external position, external of the bore of the barrel.

9. The syringe structure of claim 8 wherein the vial stop includes a projection carried by the barrel for maintaining the vial stop element in the internal position.

10. A via holding syringe structure, the vial of the type having a pierceable membrane at one end and a removable protective cap covering the pierceable membrane, the syringe structure comprising:
 a barrel having a bore, a sealable needle end and a plunger end;
 a plunger including a stem, having inner and outer ends, and a piston seal sized to sealingly engage the bore, the plunger slidably mounted within the barrel at the plunger end for reciprocal movement between a depressed position, with the inner end towards the needle end, and a retracted position, with the inner and spaced apart from the needle end, the barrel and plunger defining a variable volume region at the needle end, a partial vacuum being created in the variable volume region when the plunger moves towards the retracted position;
 the stem having an interior sized to house the vial;
 means for transferring the contents of the vial along a path to the variable volume region when the variable volume region is at the partial vacuum; and
 means for retaining the protective cap at an outer surface of the barrel;
 whereby the transferred contents of the vial in the variable volume region can be injected through a hollow needle, mounted to the needle end, by the manipulation of the plunger.

11. The syringe structure of claim 10 wherein the protective cap retainer means includes means for removing the protective cap from the vial.

12. A vial holding syringe structure, the vial of the type having a pierceable membrane at one end, the syringe structure comprising:
 a barrel having a bore, a sealable needle end, and a plunger end;
 a plunger including a stem, having inner and outer ends, and a piston sized to sealingly engage the bore, the piston being mounted to the outer end of the stem, the plunger slidably mounted within the barrel at the plunger end for reciprocal movement between a depressed position, with the inner end towards the needle end, and a retracted position, with the inner end spaced apart from the needle end, the barrel and plunger defining a variable volume region at the needle end, a partial vacuum being created in the variable volume region when the plunger moves towards the retracted position;
 the stem having an interior sized to house the vial;
 the barrel having an opening, communicating with the variable volume region, at the needle end;
 means for selectively sealing said opening; and
 means for transferring the contents of the vial along a path to the variable volume region when the variable volume region is at the partial vacuum, the transferring means including a hollow piercing member, having a piercing end, positioned within the interior of the stem opposite the pierceable membrane of the vial, and a one-way valve, formed as a part of the piston and positioned along said path to permit the contents of the vial to flow into the variable volume region;
 whereby the transferred contents of the vial in the variable volume region can be injected through a hollow needle, mounted to the needle end, by the manipulation of the plunger.

13. A medicine container holding syringe structure comprising:
 a barrel having a bore, a sealable needle end and a plunger end;
 a plunger including a stem, having inner and outer ends, and a piston sized to sealingly engage the bore, the plunger slidably mounted within the barrel at the plunger end for reciprocal movement between a depressed position, with the inner end towards the needle end, and a retracted position, with the inner end spaced apart from the needle end, the barrel and plunger defining a variable volume region at the needle end, a partial vacuum being created in the variable volume region when the plunger moves towards the retracted position;

the stem having an interior sized to house the medicine container;

the barrel having a selectively sealable opening, communicating with the variable volume region, at the needle end; and means for transferring the contents of the medicine container along a path to the variable volume region when the variable volume region is at the partial vacuum, the transferring means including a one-way valve along said path to permit the contents of the vial to flow into the variable volume region but not the reverse without any manipulation by the user, the oneway valve being formed as a part of the piston;

whereby the transferred contents of the medicine container in the variable volume region can be injected through a hollow needle, mounted to the needle end, by the manipulation of the plunger.

* * * * *